United States Patent
Grisan et al.

(10) Patent No.: US 9,629,614 B2
(45) Date of Patent: Apr. 25, 2017

(54) METHOD FOR AUTOMATICALLY MEASURING A FETAL ARTERY AND IN PARTICULAR THE ABDOMINAL AORTA AND DEVICE FOR THE ECHOGRAPHIC MEASUREMENT OF A FETAL ARTERY

(71) Applicant: UNIVERSITÀ DEGLI STUDI DI PADOVA, Padua (IT)

(72) Inventors: Enrico Grisan, Padua (IT); Elisa Veronese, Este (IT); Erich Cosmi, Padua (IT)

(73) Assignee: UNIVERSITA DEGLI STUDI DI PADOVA, Padova (IT)

( * ) Notice: Subject to any disclaimer, the term of this patent is extended or adjusted under 35 U.S.C. 154(b) by 260 days.

(21) Appl. No.: 14/376,440

(22) PCT Filed: Feb. 1, 2013

(86) PCT No.: PCT/IB2013/000125
§ 371 (c)(1),
(2) Date: Aug. 4, 2014

(87) PCT Pub. No.: WO2013/114186
PCT Pub. Date: Aug. 8, 2013

(65) Prior Publication Data
US 2015/0005636 A1    Jan. 1, 2015

(30) Foreign Application Priority Data
Feb. 3, 2012    (IT) .............................. PD2012A0026

(51) Int. Cl.
*A61B 8/08*    (2006.01)
*G06T 7/00*    (2017.01)
(Continued)

(52) U.S. Cl.
CPC .......... *A61B 8/5223* (2013.01); *A61B 8/0858* (2013.01); *A61B 8/0866* (2013.01);
(Continued)

(58) Field of Classification Search
CPC ... A61B 8/5223; A61B 8/0866; A61B 8/0891; A61B 8/14; A61B 8/0858; G06T 7/0081;
(Continued)

(56) References Cited

U.S. PATENT DOCUMENTS

| | | |
|---|---|---|
| 2003/0199762 A1 | 10/2003 | Fritz et al. |
| 2009/0136108 A1 | 5/2009 | Badiei et al. |

(Continued)

OTHER PUBLICATIONS

Elisa Veronese et alal: "<title>Estimation of prenatal aorta intima-media thickness in ultrasound examination</title>", Proceedings of SPIE, Feb. 23, 2012 (Feb. 23, 2012), pp. 83150M-83150M-8, XP55040068, ISSN: 0277-786X, DOI: 10.1117/12.911262.

*Primary Examiner* — Peter Luong
(74) *Attorney, Agent, or Firm* — Mark M. Friedman

(57) ABSTRACT

Method for automatically measuring a fetal artery, and in particular the abdominal aorta, which comprises a step for acquiring and storing a sequence cineloop of B-mode images of the fetal abdomen by means of an ultrasonographic device; a step for the approximate identification of the abdominal aorta, by means of a bank of directional filters obtaining an approximate image; a step for the fine identification for each image of said sequence, of the walls of the abdominal aorta, starting from the aforesaid approximate image by means of a calculation model based on the active contours obtaining sequences of segmented images; a step for measuring the diameter and/or the corresponding intima-media thickness of the fetal artery and in particular of the abdominal aorta, conducted at one or more segmented images.

18 Claims, 2 Drawing Sheets

(51) Int. Cl.
  *A61B 8/14* (2006.01)
  *G06T 7/11* (2017.01)
  *G06T 7/62* (2017.01)

(52) U.S. Cl.
  CPC .............. *A61B 8/0891* (2013.01); *A61B 8/14* (2013.01); *G06T 7/0012* (2013.01); *G06T 7/11* (2017.01); *G06T 7/62* (2017.01); *G06T 2207/30101* (2013.01)

(58) Field of Classification Search
  CPC ................. G06T 7/0012; G06T 7/602; G06T 2207/30101
  See application file for complete search history.

(56) References Cited

U.S. PATENT DOCUMENTS

2010/0217123 A1* 8/2010 Eran ................. A61B 8/08
  600/437
2011/0150274 A1  6/2011  Patwardhan et al.
2011/0257545 A1  10/2011  Suri

* cited by examiner

METHOD FOR AUTOMATICALLY MEASURING A FETAL ARTERY AND IN PARTICULAR THE ABDOMINAL AORTA AND DEVICE FOR THE ECHOGRAPHIC MEASUREMENT OF A FETAL ARTERY

FIELD OF APPLICATION

The present invention regards a method for automatically measuring a fetal artery, and in particular the abdominal aorta, and an ultrasonographic device for the attainment of such method, according to the preamble of the respective independent claims.

The present method and the device are intended to be employed in medicine for the processing of digital images of vascular structures, in particular for the interpretation of ultrasonographic images of fetal arteries.

Therefore, the present invention is part of medicine and diagnostic methods and devices that can be used in the medical field in order to detect, by means of instrumental investigation, the interior of organs or parts of the human body.

STATE OF THE ART

As is known, cardiovascular diseases (below referred to as CVDs for the sake of brevity) represent the third greatest cause of death in Western countries. It is therefore important, in clinical practice, to identify the early markers for the identification of any increase of risk of CVDs.

The first symptom of a possible onset of CVD is given by atherosclerosis.

The carotid artery (carotid artery, CA), both due to its anatomical position and the relatively large diameter, is particularly suitable for an examination of ultrasonographic type. From a clinical standpoint, tests are currently attained by means of known measurement devices and methods of ultrasonographic type and echo-Doppler type. Such tests are executed on the carotid artery and represent a known technique, both for a first diagnosis and for the follow-up of atherosclerotic patients. The indicator most commonly used as marker of cardiovascular and cerebrovascular risk is the thickness between the intima-media layers of the carotid.

The artery wall is constituted by three layers: the tunica intima, the tunica media and the tunica adventitia, which respectively represent the innermost, middle and outermost layer of the artery. The endothelium of the tunica intima represents the layer of the vessel in direct contact with the blood. The tunica media is mainly formed by muscular cells whose fibers are arranged transversely with respect to the length of the vessel. The tunica adventitia is constituted by bundles of connective tissue and elastic fibers.

The measurement of such intima-media thickness (referred to by the term IMT) of the carotid offers various advantages:
(i) it is a recognized early marker for the monitoring of the worsening of the atherosclerotic process;
(ii) its measurement is easily repeatable;
(iii) its measurement is non-invasive;
(iv) it is useful for quantifying the effectiveness of the disease monitoring as well as the pharmacological treatment.

Measurement devices and methods commonly employed in the evaluation of the CVDs are as said based on known ultrasonographic techniques.

Such devices and methods of known type based on the current ultrasonographic techniques reveal some drawbacks.

A first drawback lies in the fact that the quality of the images strongly depends on the ability of the operator who acquires them.

A second drawback is given by the fact that the signal to noise ratio (SNR) of the acquired images is insufficient and in particular less than that typical of other imaging techniques, such as MRI and CT.

A further drawback of the devices and methods for measuring arteries of known type lies in the difficulty of segmenting the carotid and hence defining the limit between the different layers, which are equivalent to the lumen-intima (LI) and media-adventitia (MA) interfaces.

Such drawbacks are nevertheless in part reduced by the fact that in adults the carotid is quite developed and rather superficial in order to allow fairly accurate manual measurements.

From the so-called "Barker hypothesis" (BMJ. 1995 Feb. 18; 310(6977): 411-412 "Early origin of coronary heart disease—the "Barker hypothesis"), it is known that various, typical adult diseases are caused by adaptations that the fetus performs when it is not sufficiently nourished.

Recent studies have shown that a low weight at birth, whether caused by premature delivery or depending on late intrauterine growth (referred to by the term IUGR—Intrauterine growth restriction), is associated with an increase of the rate of cardiovascular diseases and non-insulin-dependent diabetes in adult age.

It is known that in children characterized by a prenatal IUGR, the thickness of the aorta is increased, confirming the fact that the prenatal problems, such as a reduced development of the fetus, are associable to structural changes in the main vessels.

Hence, the measurement of the abdominal aIMT (referred to by the term aIMT, aortic intima-media thickness) in fetuses represents an important marker in determining the risk of atherosclerosis and more generally in determining diseases correlated to a jeopardized vascular structure.

The measurement of the intima-media thickness in the aorta aIMT in fetuses is therefore considered to be a marker in the estimation of the risk of development of atherosclerosis and other vascular diseases.

As is known, up to now both the measurement of the aIMT and that of the aortic diameter are executed manually by expert clinicians over ultrasonographic images of the fetus, by recording each measurement during the end-diastolic cardiac phase.

Manual measurement has the drawback of determining a high percentage of error, due to the variability of the measurements of the same operator or of the measurements of different operators.

The extreme difficulty in analyzing the fetal vessels, as well in acquiring ultrasonographic images of good quality, increases the percentage of error.

Indeed, while in the examinations executed by means of US on the carotid of adult subject, the position of the vessel is mainly fixed and the vessel itself represents the largest part of the image, this does not occur in the cases of fetuses.

In addition, in adult subjects the estimation of the position of the lumen and the consequent extraction of the profiles along which one can analyze the light variations is facilitated by the fact that the carotid is relatively well-aligned with the image. Finally, the fact that this is a surface vessel ensures that the acquisition of images of the carotid and the structure of its walls (tunica intima, media and adventitia) ensures a very high resolution with respect to the noise: it is known that the typical noise of US images damages any measurement that is based on the estimate of the gradient of the image itself.

In the case of fetal ultrasonographic images, however, given that the structures to be displayed are found inside the maternal uterus, the resolution of the US images is lower than that of the acquired images of the carotid of adult subjects. Besides this clear limit, there is also the fact that the size of the vessels and of the tunica intima and media layers is reduced in the fetus with respect to the adult.

For such reasons, the measurements of the aIMT and of the aortic diameter executed manually on ultrasonographic images of the fetus are still quite difficult and inaccurate as of date.

Additionally, there is the fact that the fetus moves, in a manner such that the position and orientation of the aorta are in every respect unpredictable: during acquisition, the aorta can move inside and outside the visual field of the ultrasound device.

A further problem is represented by the presence of organs and tissues that surround the aorta, and given that upon ultrasonographic examination they appear as hyperechogenic tissues which enclose hypoechogene substances (e.g. the gastrointestinal tract or the bladder, . . . ), such organs/tissues further complicate the identification of the aorta itself. Finally, the measurements of the aIMT and of the aortic diameter are affected by the cardiac cycle, which must be recognized in order to obtain uniform and meaningful measurements. The coupling of the ultrasonographic device with an electrocardiograph device (ECG) in the measurement step in order to recognize the phases of the heart, in a manner so as to execute each measurement in the same phase of the cardiac cycle, in practice revealed to be very complex due to the fact that it is difficult to precisely separate the maternal and fetal electrocardiograph signals.

Presentation of the Invention

The problem underlying the present invention is therefore that of overcoming the drawbacks revealed by the above-mentioned measurement methods and devices of known type, by providing a method for automatically measuring a fetal artery, and in particular the abdominal aorta, and an ultrasonographic device for the attainment of such method, which are precise and simple to achieve.

Another object of the present finding is to provide a method for automatically measuring a fetal artery, and in particular the abdominal aorta, and an ultrasonographic device for the attainment of such method, which are precise and simple to achieve, whose precision does not depend on the ability of the operators.

A further object of the present finding is to provide a method for automatically measuring a fetal artery, and in particular the abdominal aorta, and an ultrasonographic device for the attainment of such method, which are entirely reliable in operation.

BRIEF DESCRIPTION OF THE DRAWINGS

The technical characteristics of the invention, according to the aforesaid objects, can be observed in the contents of the claims indicated below, and the advantages thereof will be clearer in the following detailed description, made with reference to the attached drawings, which represent several purely exemplifying and non-limiting embodiments thereof, wherein:

DETAILED DESCRIPTION

Figure 1:
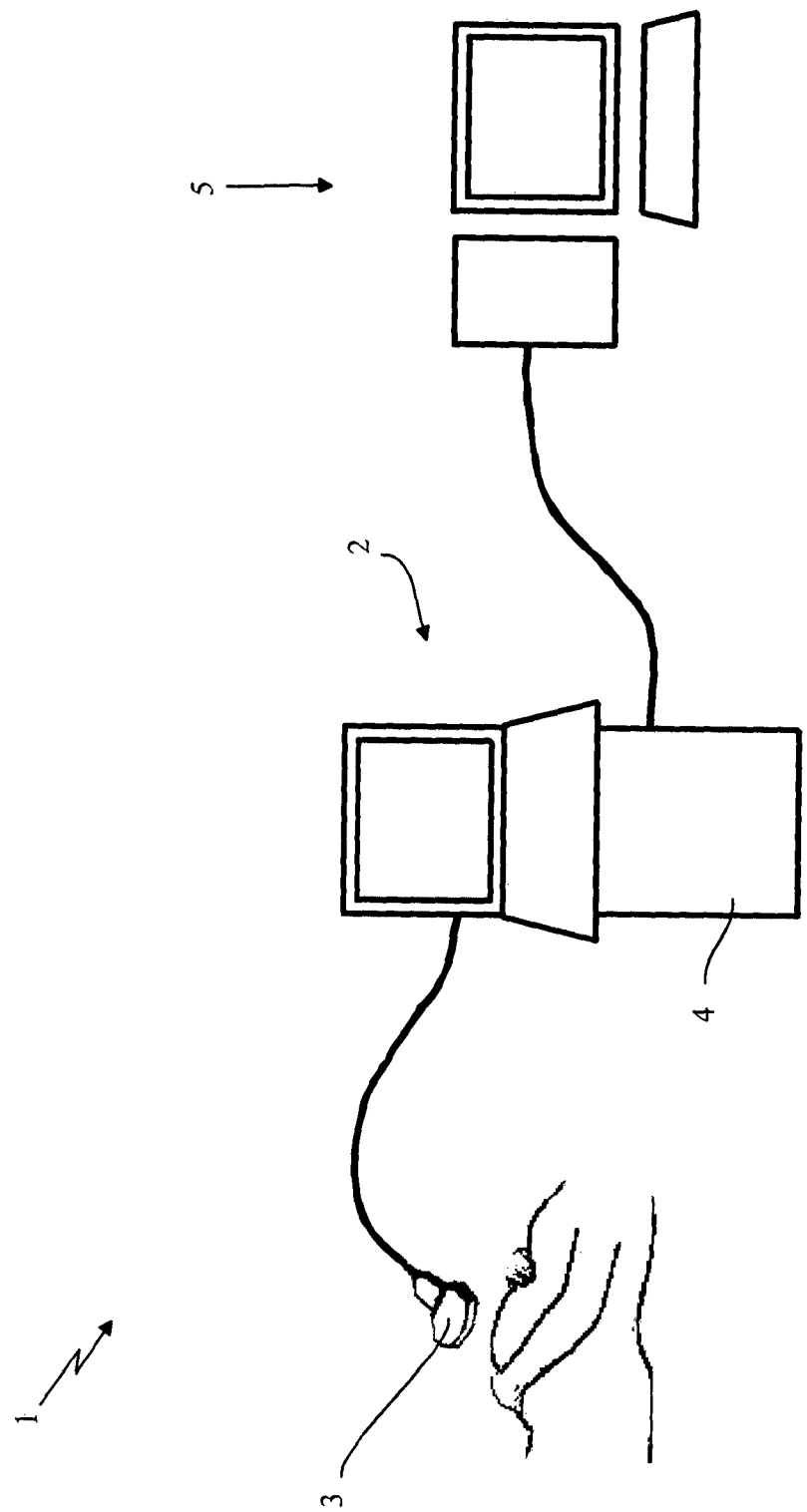
FIG. 1 shows the device for the ultrasonographic measurement of a fetal artery in an overall schematic view.
Figure 2:
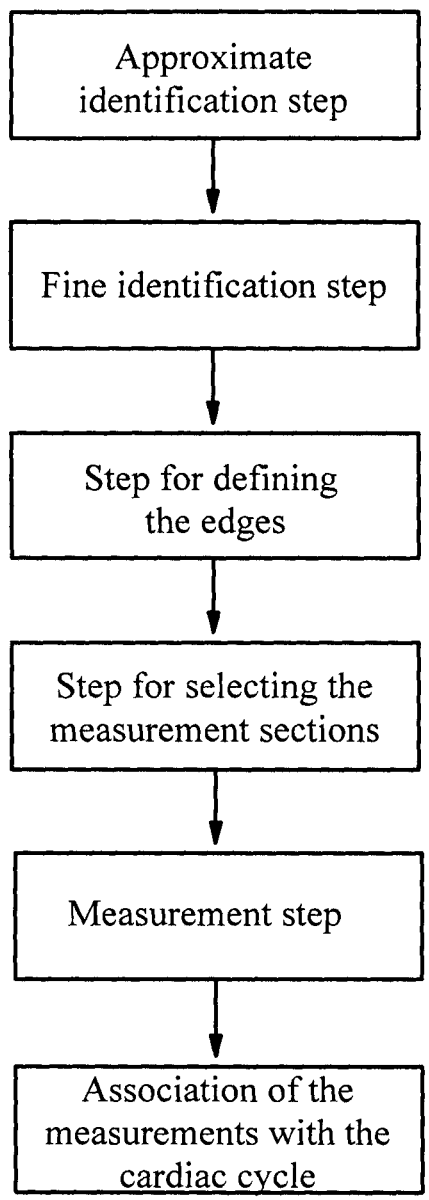
FIG. 2 represents, in a schematic manner, the flow diagram of the measurement method according to the present invention.

The method for automatically measuring a fetal artery, and in particular the abdominal aorta, object of the present invention is capable of supplying the measurement of the diameter of such artery and of the IMT (and in particular the abdominal aIMT) starting from fetal ultrasonographic images, in this manner allowing the obtainment of a quantitative, repeatable measurement of the atherosclerotic risk or risk of other vascular diseases before birth.

Below, reference will be advantageously made to the measurements on the abdominal aorta of the fetus, given that this is the artery that is best adapted to the actuation of the method, object of the present invention; nevertheless, it is intended that the method can also be applied to other arteries of the fetus without departing from the protective scope of the present patent.

As is known, the abdominal aIMT is the distance between the main edge of the blood-tunica intima interface and that of the tunica media-tunica adventitia interface in the outermost part of the vessel wall.

The aIMT can be obtained starting from the measurements of the LI (lumen-intima) and MA (media-adventitia) edges as the distance between LI and MA.

The method according to the invention provides for an initial step of acquisition and storage of at least one sequence of images of the fetal abdomen taken by means of an ultrasonographic device.

The latter is manipulated by the specialized operator on the stomach of the mother for the initial identification of the region of the fetus.

Preferably, the ultrasonographic video is acquired in a manner such that the aorta is displayed in a mainly horizontal position with respect to the orientation of the image. The size and orientation of the aorta can vary in the image plane, and the aorta itself can have a slight curvature, without jeopardizing the results of the present method.

Advantageously, the image sequence is taken by means of an ultrasonographic device capable of taking a cineloop sequence of B-mode images. It is also possible to take a cineloop sequence of three-dimensional surveys or volumes to be treated as specified below.

More in detail, ultrasonography is a known diagnostic technique that employs ultrasound. Advantageously, in the case of the present invention, it is executed with B-Mode i.e. Brightness Mode or brightness modulation.

In accordance with such mode, the echotomographic image, which represents the reflected waves coming from the organs under examination, is obtained by converting the reflected waves into signals whose brightness (gray tone) is proportional to the intensity of the single reflected waves. The spatial ratios between the different reflected waves determine the formation of the image of the organ section under examination. The white points indicate the presence of an image referred to as hyperechogenic (ultrasound quality of tissues or structures to reflect a considerable quantity of the ultrasound waves directed thereto, referring to solid structures) while the black points of a hypoechogenic image (ultrasound quality of tissues or structures to reflect very little of the ultrasound waves directed thereto, referring to liquid structures).

The B-Mode ultrasonographic images are taken in a dynamic manner, in order to supply a substantially continuous representation of the organs in real time through a sequence with a high number of images (or frames), i.e. with a sequence known in the technical jargon of the field by the term cineloop, indicating the video sequence of the images.

The method according to the invention then provides for a step for the approximate identification of the abdominal aorta of the fetus, in position and shape, by means of a bank of directional filters.

Such step produces an approximate image of the abdominal aorta of the fetus.

In order to carry out the aforesaid approximate identification of the position of the aorta, and hence also of the shape thereof, the ith frame of the video is filtered with a bank of two-dimensional directional filters k(x, y) equipped with different scales σ and orientations θ.

In accordance with a preferred embodiment of the method according to the present invention, such filters are Gabor filters, per se known and, for example, described in the article of J. G. Daugman "Uncertainty relation for resolution in space, spatial frequency, and orientation optimized by two-dimensional visual cortical filters. Journal of the Optical Society of America A, 2(7):1160-1169, July 1985" attached to the present document for reference purposes.

More generally, such filters are designed for accurately representing the boundaries between the lumen and the vascular wall of the abdominal aorta through a step for filtering at least one image of said image sequence, and preferably the first image, or one of the first images, of the image sequence, obtaining a filtered image through the use of Gaussian functions and, for example through the use of the following three Gaussian functions, for a defined number of scales and orientations:

$$k(x, y; \sigma) = -e^{-0.5[x,y]\sum_{lumen}^{-1}[x,y]^T} +$$
$$e^{-0.5[x-1.5\sigma,y]\sum_{wall}^{-1}[x-1.5\sigma,y]^T} + e^{-0.5[x+1.5\sigma,y]\sum_{wall}^{-1}[x+1.5\sigma,y]^T}$$

$$\sum_{lumen}^{-1} = \begin{bmatrix} 1/\sigma^2 & 0 \\ 0 & 1/(3\sigma)^2 \end{bmatrix}$$

$$\sum_{wall}^{-1} = \begin{bmatrix} 1/(0.25\sigma)^2 & 0 \\ 0 & 1/(3\sigma)^2 \end{bmatrix}$$

After having obtained the filtered image for a defined number of scales and orientations, a step for calculating the maximum output of the bank of filters for each pixel is provided for, through the equation:

$$I_{max}(x, y) = \max_{\sigma, \vartheta} I(x, y) * k(x, y; \sigma, \vartheta)$$

where k(x, y; σ, θ) is the filter at the scale σ rotated by an angle θ.

At this point, the image obtained $I_{max}(x, y)$ is subjected to a step of binarization by means of:

$$I_{max}(x,y) \geq t$$

with a statistical threshold $t = \mu_{I_{max}} + \sigma_{I_{max}}$, where $\mu_{I_{max}}$ and $\sigma_{I_{max}}$ represent respectively the mean and the standard deviation of the image.

Such step of binarization allows identifying the parts of the image with a higher response to the filter bank, supplying all the image parts intended to actually be the aorta, i.e. that part of the image characterized by a dark interior (the lumen) and by lighter edges (the walls).

In order to correctly identify the aorta from all the intended image parts, a step is provided for selecting the image parts having an area not smaller than a value $A_{min}$, and a marked eccentricity, so that the major axis of the aorta image is much longer than its diameter.

The calculation of the eccentricity of the aorta in all the intended image parts is for example obtained by means of the calculation of the eigenvalues of the covariance matrix of the coordinates of all the points belonging to the image part under examination, and hence by means of the calculation of the ratio of the smallest to the larges, obtaining a value in the range [0, 1].

The connected component having greater area $A_{min}$ and the highest value of eccentricity represents the image part corresponding with the aorta.

The contour of such image part represents the first estimate $AC_{i,1}$ of the shape of the aorta for the ith frame of the video.

After the step for the approximate identification of the position and the shape of the abdominal aorta of the fetus, a step is then provided for the fine identification of the walls of the abdominal aorta, starting from the approximate image of the abdominal aorta obtained in the preceding step. Such identification step is attained on each image of the sequence of images that constitute the video, by means of a calculation model based on the active contours.

Such step for the fine identification generates a sequence of segmented images.

The aforesaid step for the fine identification of the aorta passes through the refinement of the identification of the aorta walls.

Starting from the approximate image of the aorta obtained in the preceding step for the approximate identification, it is necessary to improve the definition of the contours of the edges of the vessel at the walls of the lumen of the aorta.

For such purpose, the calculation method known as "active contours" (ACs) is used. Such calculation method provides for the use of parametric curves v(s)=[x(s), y(s)], s ∈[0,1] which are deformed in the domain of the image in a manner so as to recognize the desired features of the image.

Such calculation method is per se known to the man skilled in the art and is for example described in the following three articles: C. Xu, J. L. Prince, "Snakes, shapes, and gradient vector flow." IEEE transactions on image processing 7 (3), 1998, 359-369; C. P. Loizou, C. S. Pattichis, M. Pantziaris, T. Tyllis, A. Nicolaides, "Snakes based segmentation of the common carotid artery intima media", Med. Biol. Eng. Comput. 45 (1) (2007) 35-49; and D-C Cheng, A Schmidt-Trucksäss, K-S Cheng, M. Sandrock, Q. Pu, H. Burkhardt, "Automatic Detection of the Intimal and the Adventitial Layers of the Common Carotid Artery Wall in Ultrasound B-Mode Images Using Snakes", IEEE International Conference on Image Analysis and Processing, 1999, 452-457, annexed to the present description for reference purposes.

The deformation of the curve is obtained by minimizing for example the energy functional $$E_{xy} = \int_0^1 [\tfrac{1}{2}(\alpha|v'(s)|^2 + \beta|v''(s)|^2) + E_{ext}(v(s), f(I))] ds$$

where α and β are numeric parameters with which it is possible to establish the relative weight respectively of the smoothness and of the rigidity of the contour, whereas, v'(s) and v"(s) are the first and second derivative of v(s) with respect to s. $E_{ext}$ represents the external energy which pushes the contour to desired features of the image f(I).

The external energy, used for guiding the active contour AC towards the edges of the different layers of the wall of the lumen of the abdominal aorta can, for example, be simply calculated on the basis of the gradient of the image.

On the basis only of the gradient of the image, the evolution of the AC is however not optimal since the external energy is non-zero substantially only in proximity to the edges themselves (between the lumen and media and between the different layers of the aorta wall), and thus it is able to correctly direct the evolution of the AC only if this is already situated at a position close to the edges.

Therefore, generally in order to improve the evolution of the AC and to reduce the action radius of the forces calculated on the image, i.e. of the forces adapted to collimate the ACs towards the edges of the aorta wall, various selections are possible for the calculation of the external forces and hence of the energy deriving therefrom. Such formulations can include, in a per se known manner, both forces of dynamic type and those of static type.

The static force used is based on the gradient of the image. Starting from a map of the edges of the image obtained by approaching the gradient of the image, the information regarding the presence of the edges is disclosed through the convolution with a two-dimensional vector kernel, in a manner per se known, for example as described in the article by B. Li, S. T. Acton, Active contour external force using vector field convolution for image segmentation. IEEE transactions on image processing 16 (8), 2007, 2096-106.

In order to improve the convergence and reduce the influence of the edges far from the contour, in particular at the final steps of the evolution, when it is assumed to be already near the wall of the vessel, and therefore when it is necessary to improve the properties of localization of the forces related to the external energy, the radius of the vertical field is progressively reduced, during the evolution of the AC.

Thus, the AC can be influenced by possible far edges only in the initial step of the evolution thereof.

In order to evolve the AC even in those regions where the absence of edges makes the use of the gradient ineffective, a dynamic swelling force is calculated.

Unlike the conventional formulations (described for example in the articles: "B. Li, S. T. Acton, Active contour external force using vector field convolution for image segmentation. IEEE transactions on image processing 16 (8), 2007, 2096-106; L. D. Cohen, I. Cohen, Finite-element methods for active contour models and balloons for 2-D and 3-D images, IEEE Transactions on Pattern Analysis and Machine Intelligence 11(15), 1993, 1131-1147; McInerney, D. Terzopoulos, Topologically adaptable snakes, Proceedings of IEEE International Conference on Computer Vision. 1995, 840-845") which create a constant force perpendicular to the contour, and unlike those which are based on the difference between the interior and the exterior of the region enclosed by the contour (described for example in the articles: B. Li, S. T. Acton, Active contour external force using vector field convolution for image segmentation. IEEE transactions on image processing 16 (8), 2007, 2096-106; K. Zhang, H. Song, L. Zhang, Active contours driven by local image fitting Energy, Pattern Recognition, 4(43), 2010, 1199-1206; J Mille, Narrow band region-based active contours and surfaces for 2D and 3D segmentation, Computer Vision and Image Understanding, 9(113), 2009, 946-965"), in accordance with a preferred embodiment of the method according to the present invention the dynamic force is advantageously selected perpendicular to the contour and its direction is modulated by the local difference between the gray levels inside and outside the curve at every point thereof.

Advantageously, for each point P(s) of the AC, the dynamic force is calculated by comparing the gray levels of the image in a region around P(s) outside the AC and along its normal direction n(s), with those of a region inside the AC (towards −n(s)). The result is a force that has direction given by the vector −n(s) and direction oriented towards the AC exterior or interior depending on whether, respectively, the external region of the window is darker or lighter than the internal region.

The active contour calculation method then provides for an evolution stage in which starting from the initial approximate image of the position and shape of the aorta $AC_{i,1}$ obtained by means of the step for the approximate identification, the ith frame of the image sequence has a contour that evolves under the thrust of the forces, advantageously both internal and external, related to the corresponding energies $AC_{i,t+1}=AC_{i,t}+F_{int,t}+F_{ext,t})\Delta t$ in which the index t represents the iteration and $\Delta t$ the integration step, by determining the segmentation of the aorta with final contour $AC_{i,final}$. Advantageously, for a greater computational efficiency, and assuming that the position and the shape of the aorta do not vary drastically from one frame to the next, it is preferable to use the image obtained from the final estimate of the preceding frame $AC_{i,1}=AC_{i-1,final}$, as the initial approximate image for the all the frames after the first, instead of the image obtained by means of the step for the approximate identification Starting from the sequences of segmented images obtained by means of the active contour calculation method of the step for the fine identification of the walls of the abdominal aorta, a step is then attained on each segmented image for selecting one or more measurement sections of the abdominal aorta, by means of analysis on each segmented image of the segmented image sequence of the light intensity gradient values of the image, in particular in gray scale, measured along lines orthogonal to the axis of the lumen. The subsequent measurement step is then advantageously carried out at one or more segmented images of one or more of the aforesaid measurement sections.

More in detail, the abovementioned step for selecting the measurement sections provides that, for each segmented image of the aorta $AC_{i,final}$, the skeleton of the aorta itself is calculated, i.e. the set of points on the axis of the aorta.

For each point P(s) of such axis, the light intensity values of the image (e.g. color intensity in the gray scale) are extracted along a radial line passing through P(s) and perpendicular to the axis.

Then, the sections at the lumen-intima interface are selected in which the gradient of gray levels from dark in the lumen to light in the wall, calculated along the aforesaid radial lines, is greater than a threshold value.

In other words, it occurs that the gradient along the lumen-intima interface is significantly greater than that in the inner part of the lumen, around the same wall.

The set of points of the axis P(s) for which such final conditions are verified represent the sections of the aorta in which the wall is better identifiable, and therefore all the subsequent measurements will be more reliable. The set of such sections represents the "measurement region". As discriminant, the set of points can be taken on the axis of the aorta in which such gradients along the radii are maximized, by exceeding for example a threshold value.

By extracting the light intensity values of the segmented image $AC_{i,final}$ of the radial lines passing through all the points of the axis P(s), there remain advantageously defined, for each segmented image, also the estimated edges of the tunica intima and tunica adventitia of the aorta.

The method then provides for a step for measuring the diameter and/or the corresponding intima-media thickness of the abdominal aorta, conducted at one or more of the measurement sections, and advantageously on all the measurement sections, and on one or more of the segmented images and advantageously on all the segmented images of the image sequence.

More in detail, in such measurement step the light intensity values of the image are extracted along the radial line arranged perpendicular to the axis of the artery and passing through the measurement section of the measurement region.

Then, the two vascular walls are separately analyzed (proximal and distal, i.e. diametrically opposed). For each of these walls, the profile of the gray levels of the lumen and of the vascular wall is modeled with one or more Gaussian functions.

For example, it is possible to employ three Gaussian functions, of which that with highest variance represents the brightness variation in low frequency through the vessel wall, whereas the two with lowest variance represent the layers of the vascular wall (intima-media and adventitia).

Given the model:

$$GM(x) = \sum_{j=1}^{3} z_j G_j(x; \mu_j, \sigma_j)$$

$$G(x; \mu, \sigma) = e^{-0.5(\frac{x-\mu}{\sigma})^2}$$

Where x is the position along the line passing through the point of the measurement section and perpendicular to the axis being analyzed. The parameters of GM(x) $z_j$, $\mu_j$, $\sigma_j$ must be estimated by fitting the model on the data.

Once the parameters are obtained, and supposing that $G_2$ is the Gaussian function corresponding to the intima-media and $G_3$ to the adventitia, the position of the media-adventitia interface $\hat{x}_{ma}$ is estimated as the local minimum present in the range [$\mu_2$, $\mu_3$]. Such position is deemed valid only if the difference between the local minimum and the two peaks of the model in GM($\mu_2$) and GM($\mu_3$) is greater than a threshold value $T_{rel}$. The lumen-intima interface is then calculated as the point $\hat{x}_{li}$ in which GM(x)=αGM($\mu_2$) in the range [0, $\mu_2$], with α a parameter for regulating the position along the ascending curve of the intensity at the lumen-intima interface.

For each section P(j) belonging to the measurement region of the ith segmented image, after having analyzed the light intensity profile perpendicular to the axis of the artery as described above, the positions of the lumen-intima and media-adventitia interfaces are defined, both in the proximal part ($\hat{x}_{li,prox}(j)$ and $\hat{x}_{ma,prox}(j)$)) and in the distal part ($\hat{x}_{li,dist}(j)$ and $\hat{x}_{ma,dist}(j)$), from which the diameter and the value of the aIMT are calculated as the mean of the intima-media thickness of the proximal wall and of the distal wall:

$$d_i(j) = \hat{x}_{li,prox}(j) - \hat{x}_{li,dist}(j)$$

$$aIMT_i(j) = \frac{(\hat{x}_{ma,prox}(j) - \hat{x}_{li,prox}(j)) + (\hat{x}_{ma,dist}(j) - \hat{x}_{li,dist}(j))}{2}$$

Having available N measurements of the diameter and of the IMT, it is possible to calculate, as representative value of each image, the mean values $\mu_d(i)$ and $\mu_{IMT}(i)$ thereof to which the relative standard deviation $\sigma_d(i)$ and $\sigma_{IMT}(i)$ is associated.

Advantageously, the value of aIMT to be measured is that relative to the end of systole, and therefore it is necessary to estimate the position of the various measurements relative to the cardiac cycle.

For such purpose, by taking under examination the variations of the aortic diameter recognizable along the images in sequence of the acquired image sequence, it is possible to define the parameters of a sinusoid by fitting it to the sequence of values of the diameters calculated for the aforesaid images in sequence.

Such sinusoid corresponds with the cardiac cycle; from its maximum and minimum points, it is possible to identify the images associated with the steps of systole and diastole. In particular, therefore, the measurements of the diameter and of the aIMT taken during the same systole phases of the cardiac cycle are grouped together, thus obtaining the desired measurement.

The measurement of the heart rate is also obtained together with the course of the cardiac cycle.

Should the heart rate vary during the ultrasonographic examination, the measurements associated with the systole phases of the diameter and of the aIMT may not be accurate. The aIMT is not constant during the cardiac cycle, but varies with the variation of the aortic diameter. It is therefore possible to obtain a functional relation between the two entities, in which the value of the intima-media thickness varies in relation to the diameter of the aorta:

$$aIMT(d) = p_1 - \frac{p_2}{1 - e^{(d-p_3)/p_4}}$$

Having available a number of value pairs (d, aIMT) equal to the number of frames of the video, should they be more than four it is possible to estimate the optimal parameters $p^*=[p^*_1, \ldots, p^*_4]$ of such functional relation; the estimate of such optimal parameters can be obtained with an estimate of the non-linear least squares.

The final estimate of the aIMT and its variation are obtained as:

$$aIMT^* = p^*_3,$$

$$DaIMT = (p^*_1 - p^*_2)$$

The method finally advantageously provides for attaining a fit of a curve on the data corresponding to the measurements of the aortic diameter: the curve represents the variation of the aortic diameter. This allows obtaining the maximum, the minimum and the variation speed in a single cycle. The same fit operation is executed for the data relative to the measurement of the aIMT.

In accordance with an advantageous characteristic, the method that is the object of the present invention allows determining an estimate of the stiffness of the aorta.

The stiffness of the aorta is an important parameter in the functional evaluation of the vessel and the macrocirculation. It can be obtained from the measurements carried out as:

$$aS = \max(\mu_d(i)) - \min(\mu_d(i))$$

An ultrasonographic device 1 for automatic measurements on a fetal artery, and in particular adapted for attaining the above-described measurement method, is also an object of the present invention whose same lexical references shall be maintained hereinafter for the sake of descriptive simplicity.

The measurement device 1 comprises an ultrasonographic apparatus 2, per se of a type very well known to the man skilled in the art and for this reason not described herein in detail; such ultrasonographic apparatus 2 is equipped with a probe 3 and with a unit for processing the acquired signal 4.

The probe 3 is used both for the transmission of the ultrasound waves towards the abdominal aorta that one wishes to analyze, and for the reception of the ultrasound echoes generated by the artery and by the organs adjacent thereto, which reflect the waves that hit them.

The signal processing unit 4 of the ultrasonographic apparatus 2, by means of an envelope detection operation on the signal received by means of the probe, generates the envelope of the signal required for the display of the images.

The signal processing unit 4 of the ultrasonographic apparatus 2 then acquires and stores a sequence of B-mode images.

In accordance with the idea underlying the present invention, the device for the ultrasonographic measurement 1 also comprises an electronic processing unit 5 which calculates the approximate position and shape of the abdominal aorta of the fetus, by means of a bank of directional filters, obtaining an approximate image of the abdominal aorta.

Such electronic processing unit 5 in particular works according to the step for the approximate identification of the fetal artery described above.

The electronic processing unit 5 then applies, to each image of the sequence of approximate images, the calculation model based on the active contours with an evolution stage which starts from the approximate position and shape of the abdominal aorta of the fetus (i.e. otherwise the evolution stage uses the image obtained from the final estimate of the preceding frame as initial approximate image, for the all the frames after the first), obtaining sequences of segmented images.

Such electronic processing unit 5 works in particular according to the step for the fine identification of the fetal artery described above.

The electronic processing unit 5 then analyzes the light intensity gradient measured along lines orthogonal to the axis of the lumen of the abdominal aorta for at least one segmented sequence of images, and then selects, for each segmented image, one or more measurement sections of the abdominal aorta through the values that the light intensity gradient assumes. The aforesaid selection is actuated, in particular by means of the above-described selection step, by verifying that at the trace of the edge LI of the wall, there is actually a variation of gray levels from dark (in the lumen) to light (in the wall), i.e. by selecting those sections at the lumen-intima interface in which the gradient of gray levels from dark in the lumen to light in the wall, calculated along the aforesaid radial lines, is greater than a predetermined threshold value.

The electronic processing unit 5 then measures, in particular through the above-described measurement step, the diameter and/or the corresponding intima-media thickness of the abdominal aorta, over a succession of images of the sequence of segmented images (and advantageously over the entire sequence) and preferably at one or more of the measurement sections of each segmented image.

The finding thus conceived therefore attains the pre-established objects.

Obviously, in the practical achievement thereof, it can also assume shapes and configurations that are different from that illustrated above, without departing from the present protective scope. In addition, all details can be substituted by technically equivalent elements and the shapes, sizes and materials employed can be of any type as required.

The invention claimed is:

1. Method for automatically measuring a fetal artery, and in particular the abdominal aorta, characterized in that it comprises; a step for acquiring and storing at least one sequence of images of the fetal abdomen by means of an ultrasonographic device; a step for a approximate identification of the fetal artery, and in particular of the abdominal aorta, by means of a bank of directional filters, obtaining an approximate image of the fetal artery and in particular of the abdominal aorta; a step for a fine identification of the walls of the fetal artery and in particular of the abdominal aorta, starting from said approximate image of the fetal artery and in particular of the abdominal aorta, in each image of said sequence of images by means of a calculation model based on a active contours, obtaining sequences of segmented images; a step for measuring a diameter or a corresponding intima-media thickness of the fetal artery and in particular of the abdominal aorta, conducted at one or more segmented images.

2. Method for automatically measuring a fetal artery according to claim 1, characterized in that it comprises a step for selecting one or more measurement sections of the fetal artery, and in particular of the abdominal aorta, by means of analysis on each segmented image of said sequence of segmented images of a light intensity gradient of the image, in particular in gray scale, measured along lines orthogonal to a axis of the lumen of the fetal artery and in particular of the abdominal aorta; said measurement step being carried out at one or more segmented images of one or more of said measurement sections.

3. Method for automatically measuring a fetal artery according to claim 2, characterized in that said step for selecting said measurement sections provides for: calculating a set of points on a axis of the fetal artery and in particular of the abdominal aorta, for each segmented image $AC_{i,final}$, and extracting a light intensity values of the segmented image $AC_{i,final}$ for each point $P(s)$ of such axis, along a radial line passing through $P(s)$ and perpendicular to the axis; selecting a sections at a lumen-intima interface, in which the gradient of gray levels from dark in a lumen to light in the wall, calculated along the aforesaid radial lines, is greater than a threshold value.

4. Method for automatically measuring a fetal artery according to claim 1, characterized in that said measurement step comprises: a calculation of a measurement variations of the aortic diameter or of a aIMT in segmented images placed in sequence, with a consequent determination of the course of a cardiac cycle and the determination of the segmented images corresponding to a same phase; a grouping of the measurements of the diameter and the aIMT in corresponding phases of the cardiac cycle, in particular during the systolic phases of the heart.

5. Method for automatically measuring a fetal artery according to claim 1, characterized in that said acquisition and storage step is attained by means of an ultrasonographic device for acquiring cineloop sequences of B-mode images or volumes.

6. Method for automatically measuring a fetal artery according to claim 1, characterized in that said step for the approximate identification of; a position of the abdominal aorta of the fetus is obtained with multiscale Gabor filters.

7. Method for automatically measuring a fetal artery according to claim 1, characterized in that said step for the approximate identification of; a position of the abdominal aorta of the fetus is obtained by determining; boundaries between the lumen and the vascular wall of the abdominal aorta, through: a step for filtering at least one image of said sequence of images, obtaining a filtered image through; a use of the following three Gaussian functions for a defined number of scales and orientations: a step for calculating the maximum output of the bank of filters for each pixel by means of the equation; k (x, y; $\sigma$)=--0.5 [x, y] lumen-1 [x, y] T+-0.5 [x-1.5 $\sigma$, y] wall-1 [x-1.5 $\sigma$, y] T+-0.5 [x+1.5 $\sigma$, y] wall-1 [x+1.5 $\sigma$, y] T ##EQU00006## lumen-1=[1/$\sigma$ 2 0 0 1/(3 $\sigma$) 2] ##EQU00006.2## wall-1= [1/(0.25 $\sigma$) 2 0 0 1/(3 $\sigma$) 2] ##EQU00006.3## I m ax (x, y)=m a $\sigma$, x 1 (x, y)*k(x, y; $\sigma$,) ##EQU0006.4## where k(x, y; $\sigma$, $\theta$) is the filter at the scale $\sigma$ rotated by an angle $\theta$, a step of binarization of the image that is obtained $I_{max}(x, y)$ by means of: $I_{max}(x,y) \geq t$ using a statistical threshold $t = \mu_{I_{max}} + \sigma_{I_{max}}$, where $\mu_{I_{max}}$ and $\sigma_{I_{max}}$ represent the mean and the standard deviation of the image, respectively; said step of binarization of the image by means of a threshold producing image parts intended to be the aorta having a higher response to the filter hank.

8. Method for automatically measuring a fetal artery according to claim 7, characterized in that said step for the approximate identification of the position of the abdominal aorta of the fetus comprises a step for selecting an aorta from said intended image parts by means of a selection of; image parts with area not less than a value $A_{min}$, and with a marked eccentricity.

9. Method for automatically measuring a fetal artery according to claim 1, characterized in that said step for the fine identification of the walls of the aorta, attained by means of; a active contour calculation method, provides for; a deformation of parametric curves $\nu(s)=[x(s), y(s)]s \in [0,1]$ in the domain of the obtained image, by minimizing the energy functional $E_{xy} = \int_0^1 [½(\alpha|\nu'(s)|^2 + \beta|\nu''(s)|^2) + E_{ext}(\nu(s), f(I))]ds$ where $\alpha$ and $\beta$ are numeric parameters with which it is possible to establish a relative weight respectively of the smoothness and of the rigidity of the contour, whereas, v'(s) and $\nu''(s)$ are the first and second derivative of $\nu(s)$ with respect to s and $E_{ext}$ represents the external energy which pushes the contour to desired features of the image f(I); such energy being calculated on the basis of static forces deriving from the gradient of the image and on the basis of dynamic forces perpendicular to the active contour and whose direction is modulated by the local difference between the gray levels inside and outside the curve at every point thereof.

10. Method for automatically measuring a fetal artery according to claim 9, characterized in that said dynamic force is calculated, for each point P(s) of the AC, by comparing; gray levels of the image in a region around P(s) outside the AC and along its normal direction n(s), with those of a region inside the AC (towards -n(s)), consequently defining a dynamic force that has direction given by the vector -n(s) and direction oriented towards the AC exterior or interior depending on whether the external region of the window is darker or lighter than the internal region, respectively.

11. Method for automatically measuring a fetal artery according to claim 9, characterized in that said step for the fine identification of the walls of the aorta attained by moans of the active contour calculation method provides for an evolution stage in which, the ith frame of the image sequence has a contour that, starting from the initial approximate image of the position and shape of the aorta $AC_{i,1}$ obtained by means of said preceding step for the approximate identification, evolves under the thrust of the internal and external forces related to the corresponding energies $AC_{i,t+1} = AC_{i,t} + (F_{int,t} + F_{ext,t}) \Delta t$ in which an index t represents the iteration and $\Delta t$ the integration step, by determining a segmentation of the aorta with final contour $AC_{i,final}$.

12. Method for automatically measuring a fetal artery according to claim 11, characterized in that the evolution stage of said active contour calculation method uses; a image obtained from; a final estimate of the preceding frame $AC_{i,1} = AC_{i-1,final}$ as the initial approximate image for the all the frames after the first.

13. Method for automatically measuring a fetal artery according to claim 2, characterized in that said measurement step provides for extracting a light intensity values of the segmented image along said radial lines at said measurement sections and modeling a profile of a gray levels of the lumen and of a vascular wall with one or more Gaussian functions.

14. Method for automatically measuring a fetal artery according to claim 13, characterized in that said measurement step, for each measurement section P(j) of a ith segmented image, provides for: analyzing a light intensity profile perpendicular to a axis of the fetal artery and in particular of the abdominal aorta: defining a positions of the lumen-intima interface and media-adventitia interfaces both in a proximal part ($\hat{x}_{li,prox}(j)$ and $\hat{x}_{ma,prox}(j)$) and in a distal part ($\hat{x}_{li,dist}(j)$ and $\hat{x}_{ma,dist}(j)$); calculating the diameter and a value of a aIMT as a mean of the intima-media thickness of a proximal wall and of a distal wall; $d_i(j) = \hat{x}_{li,prox}(j) - \hat{x}_{li,dist}(j)$ ##EQU00007## $aIMT_i(j) = (\hat{x}_{ma,prox}(j) - \hat{x}_{li,prox}(j)) + (\hat{x}_{ma,dist}(j) - \hat{x}_{li,dist}(j))$ 2 ##EQU00007.2## calculating a mean diameter $\mu_{d(i)}$ and aIMT $\mu_{IMT(i)}$ values of the ith segmented image, having N measurements of the diameter and the IMT available for each measurement section P(j) of the ith segmented image.

15. Method for automatically measuring a fetal artery according to claim 14, characterized in that said step for measuring the diameter and the corresponding intima-media thickness of the fetal artery and in particular of the abdominal aorta, provides for determining parameters $p^* = [p^*_1, \ldots, p^*_4]$ of a functional relation $aIMT(d) = p_1 - p_2 1 - (d - p_3)/p_4$ ##EQU00008## between the aIMT and the aortic diameter during a cardiac cycle by means of an estimate of a non-linear least squares of value pairs (d, aIMT) of corresponding images of the image sequence, a final values of the aIMT and its variation being obtained by: $aIMT^* = p^*_3$, $DaIMT = (p^*_1 - p^*_2)$.

16. Device for the ultrasonographic measurement of a fetal artery, for obtaining the method according to claim 1, which comprises: an ultrasonographic apparatus (2) equipped with a probe (3) and with a unit for processing an acquired signal (4) adapted to store a sequence of B-mode images; characterized in that said device for the ultrasonographic measurement (1) also comprises an electronic processing unit (5), which; calculates, by means of a bank of directional filters, an approximate image of the fetal artery for each image of said sequence of images; applies, to each approximate image of said sequence of images, a calculation model based on the active contours with evolution stage which, starting from said approximate image of the fetal artery, obtains segmented image sequences; calculates the light intensity gradient along lines orthogonal to the axis of the lumen of the fetal artery, on each segmented image of said sequence of segmented images, defining through values of said gradient one or more measurement sections of the abdominal aorta, measures a diameter and the corresponding intima-media thickness of the fetal artery at one or more of said measurement sections, on at least a succession of segmented images of said sequence of segmented images.

17. Method for automatically measuring a fetal artery according to claim 1, wherein said step for measuring the diameter includes measuring a corresponding intima-media thickness of the fetal artery and in particular of the abdominal aorta, conducted at one or more segmented images.

18. Method for automatically measuring a fetal artery according to claim 1, characterized in that said measurement step comprises: a calculation of a measurement variations of the aortic diameter and of a aIMT in segmented images placed in sequence, with a consequent determination of the course of a cardiac cycle and the determination of the segmented images corresponding to a same phase; a grouping of the measurements of the diameter and the aIMT in corresponding phases of the cardiac cycle, in particular during the systolic phases of the heart.

\* \* \* \* \*